United States Patent [19]

Arison et al.

[11] Patent Number: 5,478,929
[45] Date of Patent: Dec. 26, 1995

[54] BIOCONVERSION PRODUCTS OF 27-HYDROXY AVERMECTIN

[75] Inventors: Byron H. Arison, Watchung; Patrick J. Doherty, Edison; Marvin D. Schulman, Scotch Plains, all of N.J.

[73] Assignee: Merck & Co., Inc., Rahway, N.J.

[21] Appl. No.: 247,173

[22] Filed: May 20, 1994

Related U.S. Application Data

[62] Division of Ser. No. 123,181, Sep. 15, 1993, abandoned.

[51] Int. Cl.$^6$ ............................. C07H 17/08; A61K 31/70
[52] U.S. Cl. ............................. 536/7.1; 536/4.1; 435/76; 435/105; 435/119
[58] Field of Search ............................. 435/76, 105, 119; 514/30; 536/7.1, 4.1

[56] References Cited

U.S. PATENT DOCUMENTS

| | | | |
|---|---|---|---|
| 4,199,569 | 4/1980 | Chabala et al. | 514/30 |
| 4,206,205 | 6/1980 | Mrozik et al. | 514/30 |
| 4,310,519 | 1/1982 | Albers-Schonberg et al. | 514/30 |
| 4,666,937 | 5/1987 | Goegelman et al. | 514/450 |
| 4,766,112 | 8/1988 | Goegelman et al. | 514/30 |
| 5,070,015 | 12/1991 | Petuch et al. | 435/42 |
| 5,124,258 | 6/1992 | Arison et al. | 435/119 |
| 5,140,042 | 8/1992 | Arison et al. | 514/450 |
| 5,188,944 | 2/1993 | Omstead et al. | 435/76 |
| 5,192,671 | 3/1993 | Arison et al. | 435/101 |
| 5,250,422 | 10/1993 | Petuch et al. | 435/119 |

FOREIGN PATENT DOCUMENTS

| | | |
|---|---|---|
| 0194125 | 9/1986 | European Pat. Off. . |
| 0475518 | 3/1992 | European Pat. Off. . |

OTHER PUBLICATIONS

J. C. Chabala, et al., *J. Med. Chem.*, 1980, 23 pp. 1134–1136.
H. Mrozik, et al., *J. Med. Chem.*, 1982, 47, pp. 489–492.
B. H. Arison et al., *J. Antibiotics*, 46, No. 6, pp. 1016–1019 (1993).
*Chemical Abstracts*, 121, AB No. 103765.

*Primary Examiner*—David T. Fox
*Assistant Examiner*—Howard C. Lee
*Attorney, Agent, or Firm*—Sylvia A. Ayler; Mark R. Daniel

[57] ABSTRACT

There are disclosed novel compounds which are derived from 22,23-dihydro avermectin B1 aglycone. The compounds are both isomers of the 27-hydroxy adduct of the substrate avermectin compound that have been glycosylated at the 4" position to yield 4"-O-glucosyl 27-OH avermectin compounds. The compounds and the intermediates used to make them are highly potent antiparasitic, insecticidal and anthelmintic avermectin agents.

3 Claims, 4 Drawing Sheets

BIOCONVERSION PRODUCTS OF 27-HYDROXY AVERMECTIN

This application is a division of application Ser. No. 08/123,181, filed Sep. 15, 1993, now abandoned.

BACKGROUND OF THE INVENTION

Avermectin compounds are known antiparasitic agents of considerable activity. The preparation of the natural material products, the 22, 23 dihydro derivatives and the monosaccharide and aglycone derivatives are known and described in U.S. Pat. Nos. 4,320,519, 4,199,569 and 4,206,205, respectively. The preparation of hydroxylated avermectin aglycones is also known. In particular, U.S. Pat. No. 4,666,937 describes a process for producing 27-hydroxy avermectin aglycone derivatives which employs the microorganism Cunninghamella blakesleeana and produces low yields of only one stereoisomer of the 27-hydroxy compounds. Additionally, U.S. Pat. No. 5,140,042 describes the biotransformation process of producing 28-hydroxy derivatives of ivermectin aglycone using Saccharopolyspora (S.) erythrea. The hydroxylation at C28 with S. erythrea occurs with ivermectin aglycone as the substrate and not with avermectin B1 a aglycone. The instant process is significantly different in that S. erythrea is used to hydroxylate both ivermectin aglycone and avermectin aglycone at the C27 position and yields both stereoisomers (designated A and B isomers) with either compound. Additionally, both 27-OH avermectin aglycone isomers are derivatized to dissacharides and then further glycosylated to yield novel 4"-O-glucosyl 27-OH compounds.

SUMMARY OF THE INVENTION

The instant invention is concerned with the bioconversion of avermectin compounds into both A and B isomers of 27-hydroxy avermectin aglycones by feeding avermectin aglycone to fermentations with Saccharopolyspora erythrea and mutants thereof blocked in macrolide biosynthesis and derivatizing the resultant 27-OH avermectin aglycone isomers through a series of glycosylation steps to yield novel 4"-O-glucosyl 27-OH avermectin compounds. The A isomer is more active than the B isomer as an insecticide and nematocide, particularly effective against the large bowel worm, T. Sigmodontis when it is derivatized to yield the 4"-O-glucosyl 27-OH avermectin compounds. Thus it is an object of this disclosure to provide a novel method for the preparation of both isomers of 27-hydroxy avermectin aglycones. Another object is to describe the novel compounds of the instant invention. A further object is to describe the microorganism used to prepare such compounds and the fermentation conditions applicable to such bioconversion. Further objects will become apparent from reading the following description.

BRIEF DESCRIPTION OF THE DRAWING

FIG. 1 is the spectrum for the A isomer and FIG. 2 is the spectrum for the B isomer. Table 1, below, shows the pertinent chemical shifts in epimeric 27-hydroxy aglycones of FIGS. 1 and 2. The chemical shifts of H-25, H-27, 28-methyl and H-17 are diagnostic for distinguishing the epimers.

TABLE 1

| Compound | H-27 | 28-$CH_3$ | H-25 | H-17 |
| --- | --- | --- | --- | --- |
| Isomer A | 3.85 | 1.30 | 3.75 | 3.91 |
| Isomer B | 4.06 | 1.25 | 3.52 | 3.72 |

Figure 1:
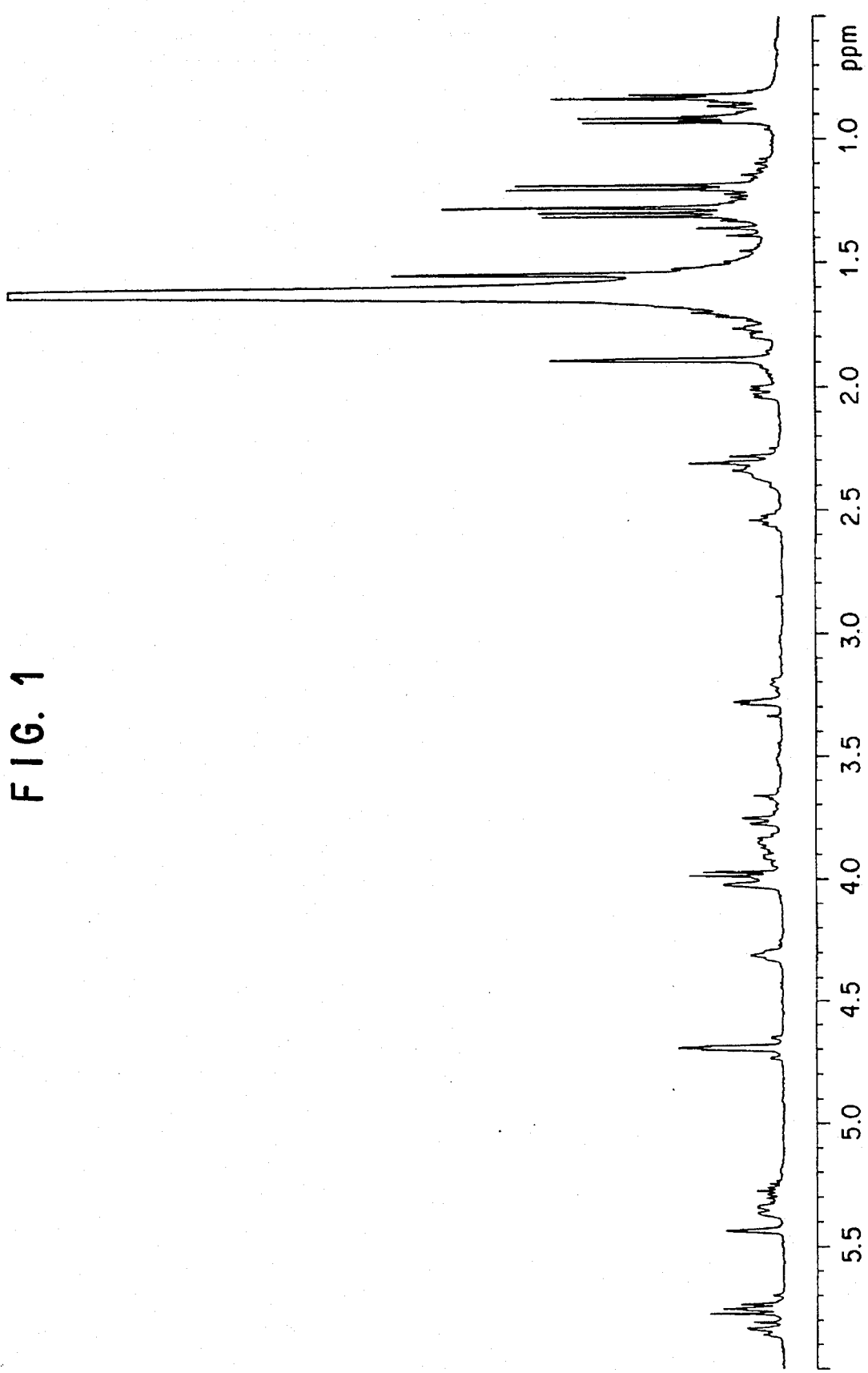
FIGS. 1 and 2 show the NMR spectra of the isomers of 27-hydroxy ivermectin aglycone.
Figure 2:
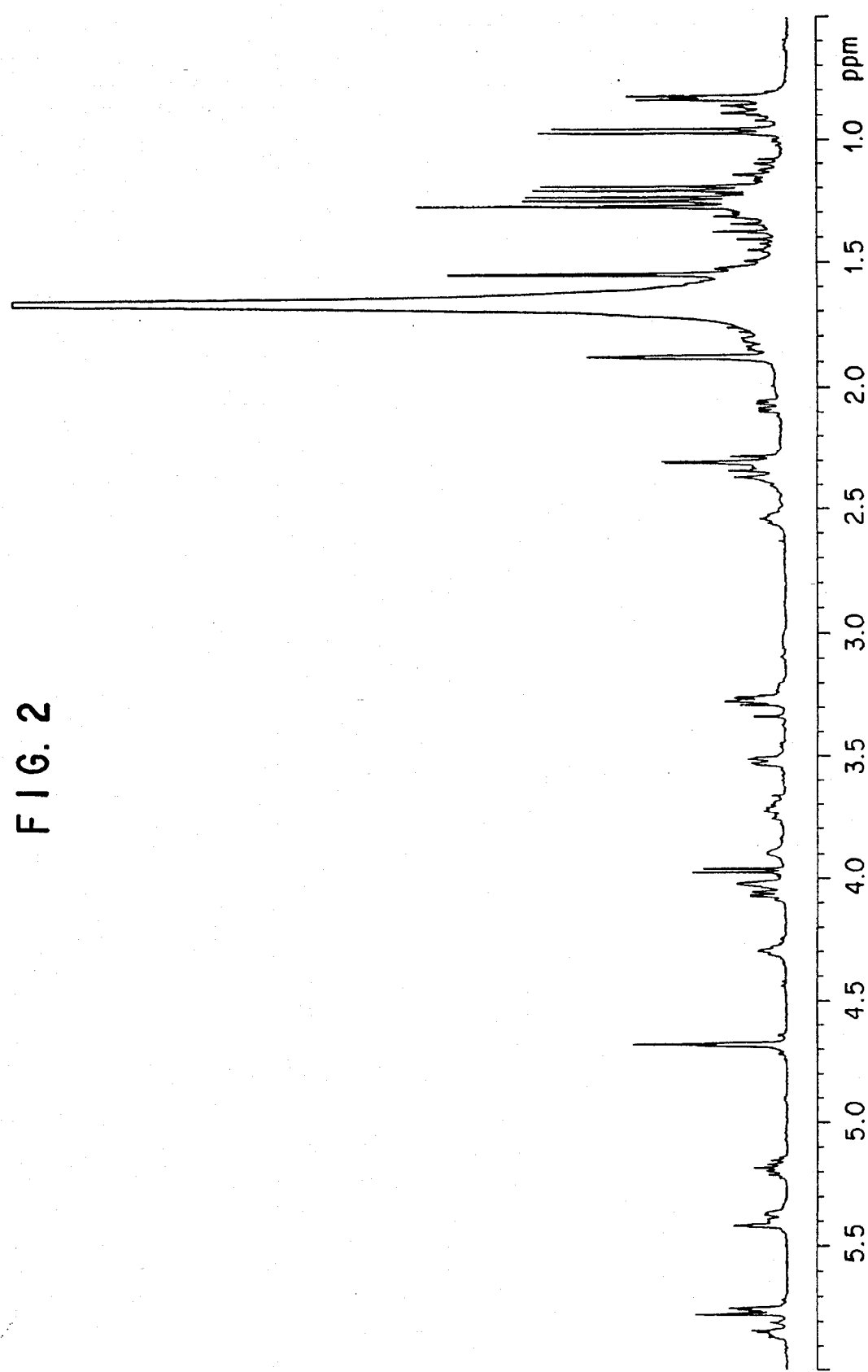
Figure 3:
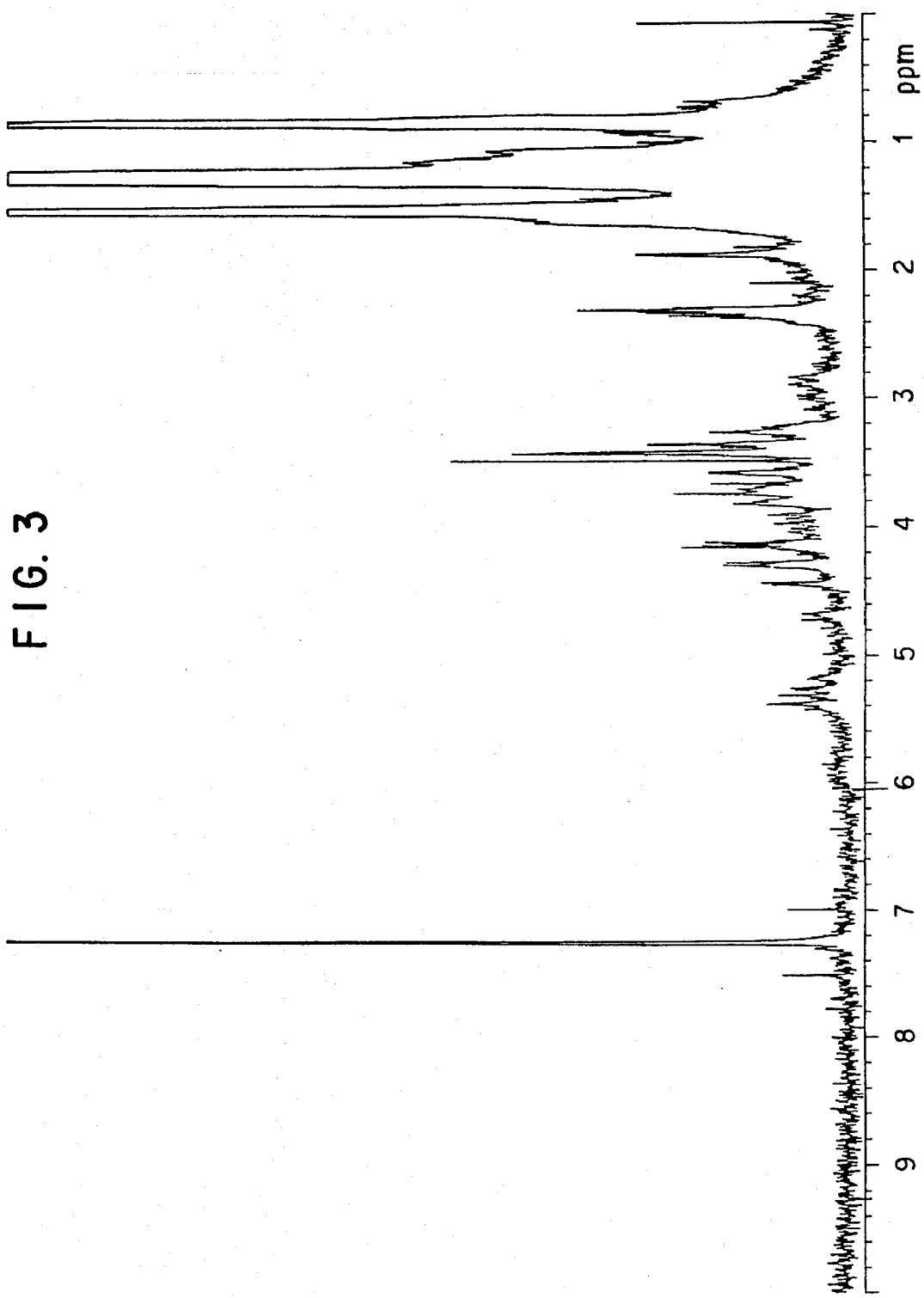
Figure 4:
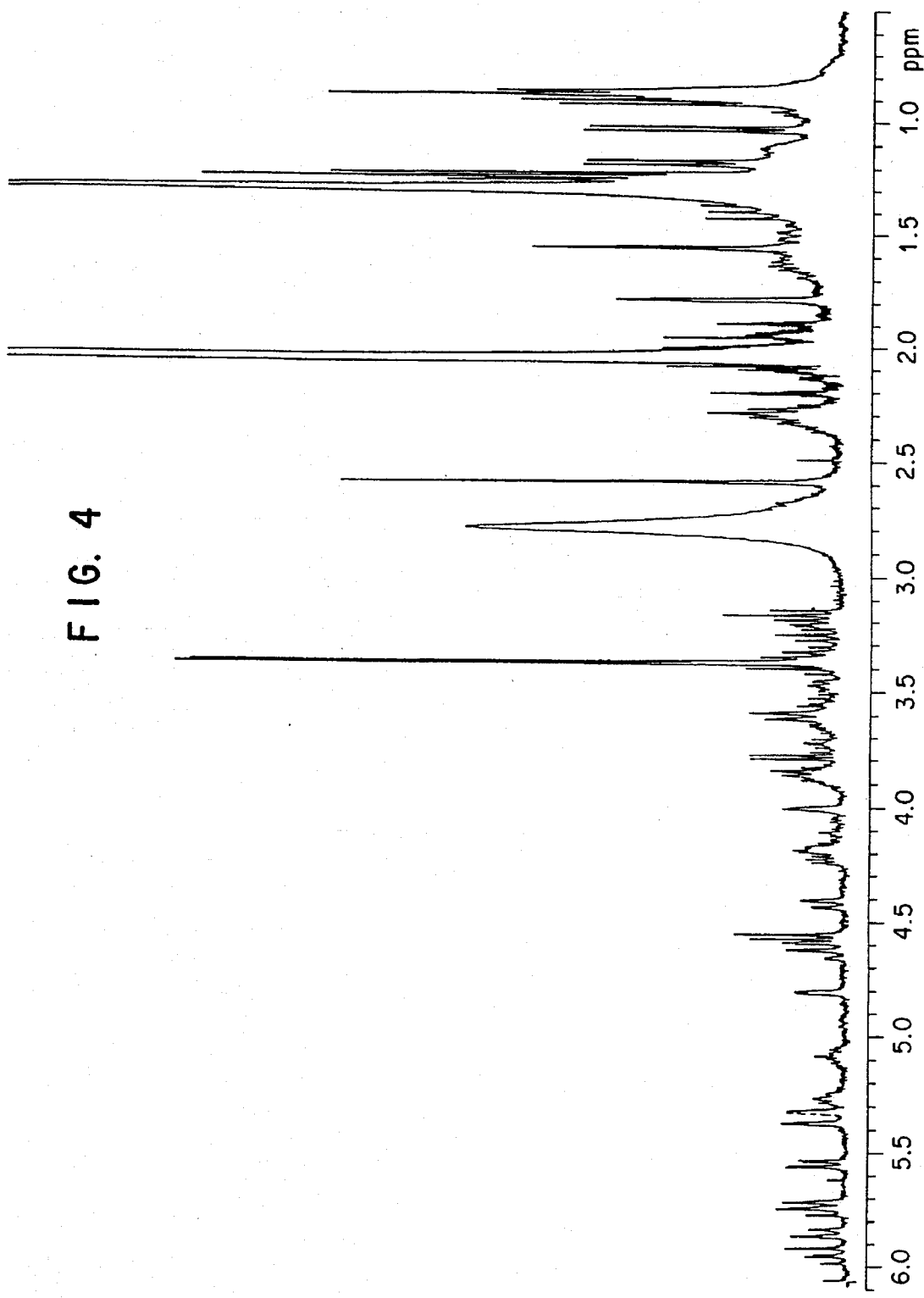

FIGS. 3 and 4 represent the nmr spectra of 4"-O-glucosyl, 27-OH -22,23 dihydro B1a isomer A and 4"-O-glucosyl, 27-OH-22,23 dihydro B 1 a isomer B, respectively.

DETAILED DESCRIPTION OF THE INVENTION

The present invention is concerned with novel 4"-O-glucosyl 27-OH avermectin compounds. This invention also concerns a novel process for making both isomers, A and B, of 27-OH avermectin aglycones (the intermediates used to make the instant compounds) in approximately 40% yields (20% of each) by adding to a fermentation medium of Saccharopolyspora ervthrea or a mutant thereof blocked in macrolide biosynthesis, a known quantity of avemectin aglycone or ivermectin aglycone.

The avermectin compounds employed as starting materials in the present invention are known potent antiparasitic agents against endoparasites and ectoparasites. The basic naturally occurring avermectins are a series of macrocyclic lactones which are substituted at position 13 with a disaccharide consisting of two oleandrose residues. See for example, U.S. Pat. No. 4,310,519. The preparation and properties of synthetic avermectin aglycones in which the disaccharide moiety has been removed leaving a free hydroxyl group at position 13 have been described by Mrozik et al., J. Org. Chem. 1982, 47, 489–492 and by Chabala et al., J. Med. Chem. 1980, 23, 1134–1136. The avermectin natural products have the following general structure:

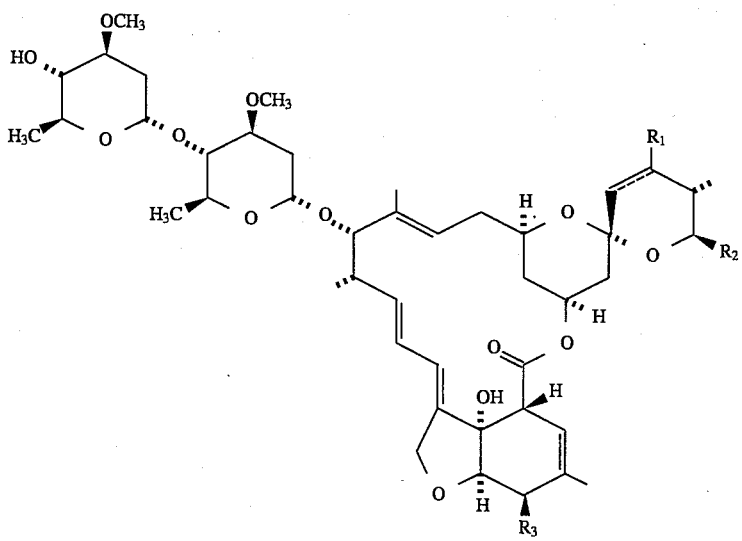

wherein the broken line at the 22,23-position indicates a single or double bond and:

$R_1$ is hydroxy and is present only when said broken line indicates a single bond;

$R_2$ is isopropyl or sec-butyl; and $R_3$ is methoxy or hydroxy.

Them are eight major natural avermectin compounds, designated A1a, A1b, A2a, A2b, B1a, B1b, B2a and B2b. These designations are based on the structure of the individual compounds as shown in the following table (referring to the foregoing structural formula).

| Compound | 22,23-bond | $R_1$ | $R_2$ | $R_3$ |
|---|---|---|---|---|
| A1a | double bond | — | sec-butyl | —OCH$_3$ |
| A1b | double bond | — | isopropyl | —OCH$_3$ |
| A2a | single bond | —OH | sec-butyl | —OCH$_3$ |
| A2b | single bond | —OH | isopropyl | —OCH$_3$ |
| B1a | double bond | — | sec-butyl | —OH |
| B1b | double bond | — | isopropyl | —OH |
| B2a | single bond | —OH | sec-butyl | —OH |
| B2b | single bond | —OH | isopropyl | —OH |

The avermectins are generally isolated as mixtures of the a and b components (typically ≧80% a and ≦20% b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components may be indicated by dropping the a or b from the designation of the compound. A mixture of avermectin B1a and avermectin B1b is thus referred to as avermectin B1. Alternatively a slash(/) is inserted between the compound designations to indicate a mixture such as in "B1a/B1b".

The above structural formula is shown without a definitive stereochemistry at certain positions and with a defined stereochemistry at other positions. However, during the course of the synthetic procedures used to prepare such compounds, or using racemization or epimerization procedures known to those in the art, the products of such procedures can be a mixture of stereoisomers. In particular, the stereoisomers at the 13- and 23-positions may be oriented either α- or β-representing such groups being below or above the general plane of the molecule, respectively.

The avermectin compounds useful as starting material in the present invention are the aglycone derivatives where the 13 position is not substituted with the two oleandrose residues, but rather with an hydroxy group. Particularly, the aglycone derivatives are avermectin aglycones with a double bond present at the 22,23 positions or Ivermectin aglycones (22,23 dihydro avermectin) with a single bond present at the 22,23 positions.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Coopefta, Ascaris, Bunostomum, Oesophagostomum, Chabertia, Trichuris, Stongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Coopefta, and Oesophagostomum attack primarily the intestinal tract while others, such as Haemonchus and Ostertagia, are more prevalent in the stomach while others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp. in cattle, Gastrophilus in horses, and Cuterebra sp. in rodents.

The instant compound is also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra intestinal stages of the intestinal worms Strongyloides and Trichinella. The compound is also of value against arthropods parasitizing man, biting insects and other dipterous pests causing annoyance to man, particularly effective against the large bowel worm, T. Sigmodontis.

The instant compound is also active against household pests such as the cockroach, Blatella sp., clothes moth, Tineola sp., carpet beetle, Attagenus sp. and the housefly Musca domestica.

The compound of the present invention is also useful against insect pests of stored grains such as Tribolium sp., Tenebrio sp. and of agricultural plants such as spider mites, (Tetranychus sp.), aphids, Acyrthiosiphon migratory orthopterans such as locusts and immature stages of insects living on plant tissue. The compound is useful as a nematocide for the control of soil nematodes and plant parasites such as Meloidogyne spp. which may be of importance in agriculture.

The instant compound can be administered orally in a unit dosage form such as a capsule, bolus or tablet, or as a liquid drench that is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to about 0.5% by weight of the active compound. Preferred drench formulations may contain from about 0.01 to about 0.1% by weight. The capsules and boluses comprise the active ingredient admixed with a carrier vehicle such as starch, talc, magnesium stearate, or dicalcium phosphate.

Where it is desired to administer the compound of the present invention in a dry, solid unit dosage form, capsules, boluses or tablets containing the desired amount of the instant compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the compound of the present invention is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol, formal and aqueous parenteral formulations are also used. The compound of the present invention is dissolved or suspended in the parenteral formulation for administration; such formulations generally contain from about 0.55% to about 5% by weight of the instant compound.

Although the compound of this invention finds its primary use as an antiparasitic agent in the treatment and/or prevention and treatment of diseases caused by parasites, for example, arthropod parasites such as ticks, lice, fleas, mites and other biting insects in domesticated animals and poultry, they are also effective in treatment of parasitic diseases that occur in other animals including humans. The optimum amount to be employed for best results will, of course, depend upon the species of animal to be treated and the type and severity of parasitic infection or infestation. Generally, good results are obtained with our novel compound by the oral administration of from about 0.001 to about 10 mg per kg of animal body weight, such total dose being given at one time or in divided doses over a relatively short period of time such as 1–5 days. With the novel compound of the present invention, excellent control of such parasites is obtained in animals by administering from about 0.025 to about 0.5 mg per kg of body weight in a single dose. Repeat treatments are given where required to combat re-infections and are dependent upon the species of parasite and the husbandry techniques being employed. The techniques for administering these materials to animals are known to those skilled in the veterinary field.

When the compound described herein is administered as a component of the feed of the animals, or dissolved or suspended in the drinking water, compositions are provided in which the active compound is intimately dispersed in an inert carder or diluent. By inert carder is meant one that will not react with the antiparasitic agent and one that may be administered safely to animals. Preferably, a carrier for feed administration is one that is, or may be, an ingredient of the animal ration.

Suitable compositions include feed premixes or supplements in which the instant compound is present in relatively large amounts and which are suitable for direct feeding to the animal or for addition to the feed either directly or after an intermediate dilution or blending step. Typical carriers or diluents suitable for such compositions include, for example, distillers' dried grains, cornmeal, citrus meal, fermentation residues, ground oyster shells, wheat shorts, molasses solubles, corn cob meal, edible bean mill feed, soya grits, crushed limestone and the like. The compound of the present invention is intimately dispersed throughout the carrier by methods such as grinding, stirring, milling or tumbling. Compositions containing from about 0.005% to about 2.0% by weight of the instant compound are particularly suitable as feed premixes. Feed supplements, which are fed directly to the animal, contain from about 0.0002% to about 0.3% by weight of the instant compound.

Such supplements are added to the animal feed in an amount to give the finished feed the concentration of active compound desired for the treatment and control of parasitic diseases. Although the desired concentration of the compound of the present invention will vary depending upon the factors previously mentioned as well as upon the particular compound employed, the compound of this invention is usually fed at concentrations of between about 0.00001% to about 0.002% in the feed in order to achieve the desired antiparasitic result.

In addition, where the compound is to be added to an animal's feed, it is possible to utilize the dried mycelial cake from the fermentation broth. The mycelia contain a preponderance of the activity and since the level of the activity of the mycelia can be determined, it can be added directly to the animal's feed.

The compound of this invention also is useful in combating agricultural pests that inflict damage upon crops while they are growing or while in storage. The compound is applied using known techniques as sprays, dusts, emulsions and the like, to the growing or stored crops to effect protection from such agricultural pests.

The anthelmintic activity of the instant compound may be determined by orally administering via the feed, a sample of the individual compound, a mixture of such compound, a concentrated extract, and the like to a mouse which had been infected 3 days earlier with a gastrointestinal parasite. At 11, 12 and 13 days after the initiation of the medication, the feces of the mouse are examined for eggs, and on the next day the mouse is sacrificed and the number of worms present in the proximal portion of the small intestine are determined. An active compound is observed when there is a significant reduction of egg and worm counts when compared to infected, unmedicated controls.

The novel 4"-O-glucosyl 27-OH B1a compounds of the instant invention are prepared in a 3 step process wherein Step 1 consists of the novel process of making both isomers of 27-OH avermectin aglycones (Hydroxylation at C27), Step 2 consists of a glycosylation with an oleandrose dissaccharide at the C 13 position (Glycosylation at C13) and Step 3 consists of a glycosylation at the C4" position which provides the compound of interest. The process is depicted in the structural diagram below.

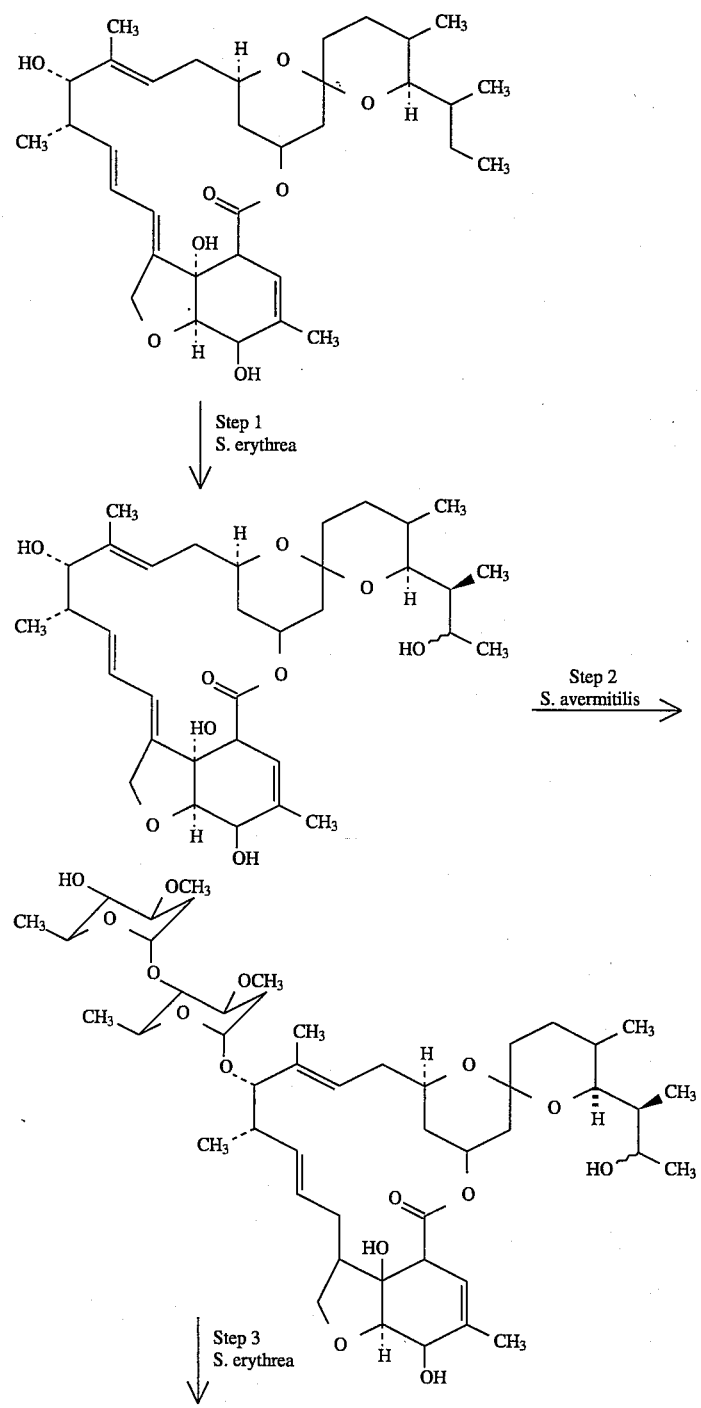

-continued

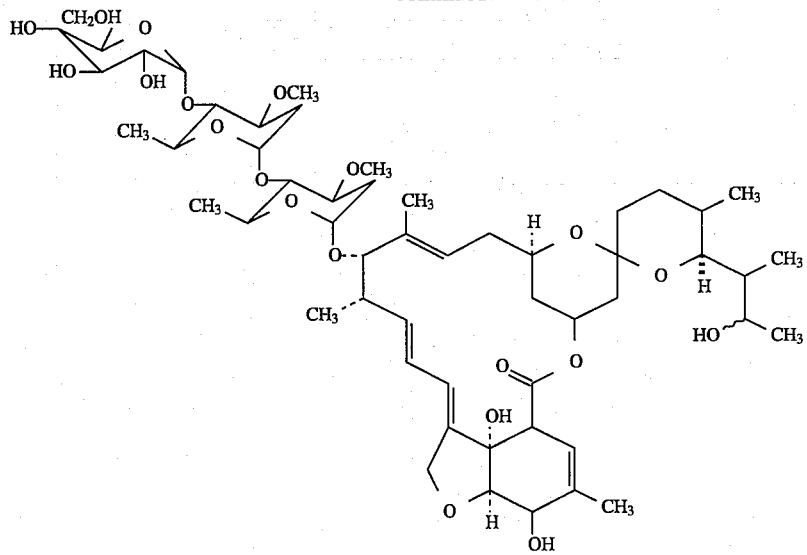

STEP 1: HYDROXYLATION AT C27

S. erythrea is a known organism and culture deposits are available, for instance, from American Type Culture Collection (ATCC). The instant invention utilizes S. erythrea strain MA1625 and mutant strain (non-erythromycin producing) MA6224, which are publicly available from the ATCC at 12301 Parklawn Drive, Rockville, Md. 20852 under the accession numbers ATCC 11635 and 31772, respectively. S. erythrea non-erythromycin producing mutant strain MA6190 is also employed in the instant invention and is publicly avalailable from the U.S. Department of Agriculture's Northern Regional Research Laboratory (NRRL) at Peoria, Illinois under the accession number NRRL 3887. Included within the scope of this invention are other strains of S. erythrea and mutants produced by natural selection or by mutating agents such as, for example, x-ray irradiation, ultraviolet radiation, nitrogen mustard or like treatments.

The fermentation is carded out in a medium containing S. erythraea and results in the production of 27-hydroxy avermectin B1 aglycone and/or 27ohydroxy ivermectin aglycone having the formula:

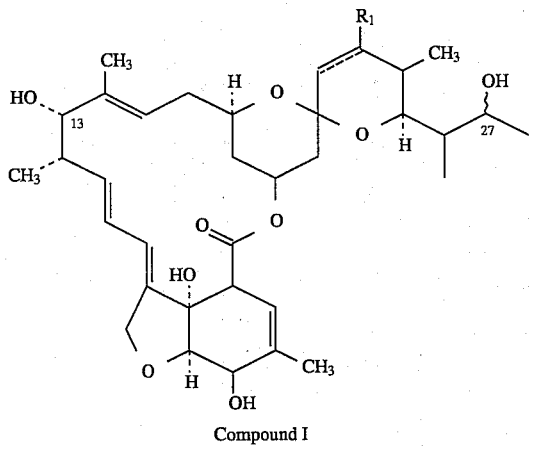

Compound I

Wherein the broken line at the 22,23 position indicates a single or double bond, $R_1$ is present only when the broken line is a single bond, $R_1$ is hydrogen and the wavey line at the 27 position represents both A and B isomers.

The instant compounds are produced during the aerobic fermentation of suitable aqueous nutrient media under conditions described hereinafter, with a producing or a non-producing mutant strain of S. erythrea. Aqueous media such as those used for the production of many antibiotic substances are suitable for use in the process for the production of this macrocyclic compound.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example glucose, sucrose, maltose, lactose, dextran, cerelose, corn meal, oat flour, and the like, and starches are suitable sources of assimilable carbon in the nutrient media. The exact quantity of the carbon source which is utilized in the medium will depend, in pan, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by S. erythrea, in the production of the instant compounds. The various sources of nitrogen can be used alone or in combination in amounts ranging from 1 to 5 g/l in the medium.

Among the nutrient inorganic salts which can be incorporated in the culture media are the customary salts capable of yielding sodium, potassium, magnesium, ammonium, calcium, phosphate, sulfate, chloride, carbonate, and like ions. Also included are trace metals such as iron, zinc, manganese, copper, boron, molybdenum and the like.

It should be noted that the media described hereinbelow and in the Examples are merely illustrative of the wide variety of media, which may be employed, and are not intended to be limiting.

The following are examples of media suitable for growing strains of Saccharopolysporaerythrea MA1625, ATCC 11635; MA6224, ATCC 31772; and MA6190 NRRL 3887:

COMPOSITION OF MEDIA

MEDIUM 1

| | |
|---|---|
| Glucose | 50 g |
| NaCl | 5 g |
| $(NH_4)_2SO_4$ | 2 g |
| $CaCO_3$ | 6 g |
| Soya Flour Extract | 30 g |
| Distilled Water | 1000 ml |
| Adjust pH to 7.0 | |

MEDIUM 2

| | |
|---|---|
| Dextrose | 20 g |
| Peptone | 5 g |
| Meat Extract | 5 g |
| Primary Yeast | 3 g |
| NaCl | 5 g |
| $CaCO_3$ | 3 g |
| Distilled Water | 1000 ml |
| Adjust pH to 7.0 | |

MEDIUM 3

| | |
|---|---|
| Soluble Starch | 10 g |
| Ardamine pH | 5 g |
| NZ amine E | 5 g |
| Beef Extract | 3 g |
| $MgSO_4 \cdot 7H_2O$ | 0.5 g |
| Cerelose | 1.0 g |
| $Na_2HPO_4$ | 0.190 g |
| $KH_2PO_4$ | 0.182 g |
| $CaCO_3$ | 0.05 g |
| Distilled Water | 1000 ml |

MEDIUM 4

| | |
|---|---|
| Cerelose | 10 g |
| Corn Starch | 40 g |
| Glycine | 7.5 g |
| Tyrosine | 0.9 g |
| Triolein | 2.5 g |
| NaCl | 2.0 g |
| $K_2HPO_4$ | 1.56 g |
| $KH_2PO_4$ | 0.78 g |
| $MgSO_4 \cdot 7H_2O$ | 0.5 g |
| $CaCl_2 \cdot 6H_2O$ | 0.001 g |
| $FeSO_4 \cdot 7H_2O$ | 0.02 g |
| $MnCl_2 \cdot 4H_2O$ | 0.001 g |
| $ZnSO_4 \cdot 7H_2O$ | 0.05 g |
| $CaCO_3$ | 3.0 g |
| Distilled Water | 1000 ml |

MEDIUM 5 (SLANT)

| | |
|---|---|
| Yeast Extract | 4 g |
| Malt Extract | 10 g |
| Dextrose | 4 g |
| Bacto Agar | 20 g |
| Distilled Water | 1000 ml |
| pH 7.0 | |

MEDIUM 6

| | |
|---|---|
| Cerelose | 15 g |
| Soybean meal | 15 g |
| $CaCO_3$ | 1.0 g |
| Distilled Water | 1000 ml |
| Adjust pH to 7.0–7.2 | |

The fermentation employing S. erythrea can be conducted at temperatures ranging from about 20° C. to about 40° C. For optimum results, it is most convenient to conduct these fermentations at a temperature in the range of from about 24° C. to about 36° C. Temperatures of from about 28° C. to about 34° C. are most preferred. The pH of the nutrient medium suitable for producing the instant compounds can vary from about 6.5 to about 8.0 with a preferred range of from about 6.8 to about 7.3.

The avermectin aglycone starting compound is added to the fermentation of S. erythrea in quantities of from about 0.1 to about 1.0 g per liter of fermentation medium. It is preferred to use from about 0.1 to about 0.5 g per liter. The avermectin aglycone compound may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the ivermectin aglycone starting compound be added to the fermentation before 50% of the cycle is completed, preferably before 25% of the cycle is completed.

Small scale fermentations are conveniently carried out by placing suitable quantities of the nutrient medium in a flask employing known sterile techniques, inoculating the flask with either spores or vegetative cellular growth of S. erythrea, loosely stoppering the flask with cotton and permitting the fermentation to proceed in a constant room temperature of about 30° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of S. erythrea. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (LPM) of air.

The separation of both isomers of the 27-hydroxy ivermectin from the whole fermentation broth and the recovery of the compound is carried out by solvent extraction and application of chromatographic fractionations with various chromatographic techniques and solvent systems.

The instant compounds have slight solubility in water, but are soluble in organic solvents. This property conveniently may be employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compounds as well as other substances lacking the antiparasitic activity of the instant compound. If the solvent is a water immiscible one, the layers are separated and the organic solvent is concentrated under reduced pressure. The residue is placed onto a chromatography column preferably containing silica gel. The column retains the desired product and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compound.

The use of the foregoing techniques as well as others known to those skilled in the art will afford purified compositions containing the instant compound. The presence of the desired compound is determined by analyzing the various chromatographic fractions for biological activity of physico-chemical characteristics. Both isomers of the instant 27-OH avermectin aglycone compounds have been determined by detailed analysis of the various spectral characteristics of the compounds, in particular their nuclear magnetic resonance, mass, ultraviolet and infrared spectra.

STEP 2: GLYCOSYLATION AT C13

The 27-OH avermectin aglycones generated above are then used as intermediates for the final product of other significantly potent antiparasitic avermectins such as the novel 4"-O-glucosyl 27-OH avermectin compounds of the instant invention, which themselves have significant parasiticidal activity as an anthelmintic, insecticide and ascaricide, particularly active against the large bowel worm, Trichostrongylus Sigmodontis in human and animal health and in agriculture. Both 27-OH ivermectin aglycone isomers of the instant invention are derivatized as the dissacharide by addition of an oleandrose disaccharide at the C13 position. The A isomer of the glucosyl 27-OH avermectin compounds, which is derived from the glycosylation of the 27-OH ivermectin aglycone is more biologically potent than that derived from the B isomer (see Tables 2 and 3 below).

TABLE 2

Anthelmintic activity of 27-OH ivermectins

| | Trichostrongylus colubriformis | Haemonchus contortus | Trichostrongylus sigmodontis |
|---|---|---|---|
| Isomer A | | | |
| 0.25 mg/kg | A* | A* | A* |
| 0.125 mg/kg | A* | A* | A* |
| 0.0625 mg/kg | A* | A* | I |
| Isomer B | | | |
| 0.25 mg/kg | A* | A* | I |
| 0.125 mg/kg | A* | A* | I |
| 0.0625 mg/kg | M | I | I |

A* = highly active; M = moderately active; I = inactive

TABLE 3

Insecticidal activity of 27-OH ivermectins

| | Lucilla larva 24 hrs | Lucilla larva 48 hrs |
|---|---|---|
| Isomer A | | |
| 1 ppm | I | A* |

TABLE 3-continued

Insecticidal activity of 27-OH ivermectins

| | Lucilla larva 24 hrs | Lucilla larva 48 hrs |
|---|---|---|
| 0.5 ppm | I | A* |
| Isomer B | | |
| 1 ppm | I | I |
| 0.5 ppm | I | I |

A* = highly active; M = moderately active; I = inactive

The 27-OH ivermectin aglycone isomers are glycosylated via a bioconversion process whereby both A and B isomers of the 27OH avermectin aglycones are fed to fermentations containing Streptomyces avermitilis MA 6941 ATCC 55292 (deposited at the American Type Culture Collection located at 12301 Parklawn Dr., Rockville, Md. 20852). The media employed in the practice of this invention for growing S. avermitilis MA 6941 ATCC 55292 by fermentations are described below.

FERMENTATION CULTURE:

| | Per Liter |
|---|---|
| Seed Medium - A | |
| Difco yeast extract | 20.0 g |
| Hycase S.F. | 20.0 g |
| Dextrose | 20.0 g |
| $KNO_3$ | 20 g |
| NaCl | 0.5 g |
| $MnSO_4.H_2O$ | 0.005 |
| $ZnSO_4.H_2O$ | 0.01 |
| $CaCl_2.H_2O$ | 0.02 |
| $FeSO_4.H_2O$ | 0.025 |
| pH = 7.0 | |
| Biotransformation Medium | |
| Peptonized Milk | 17.5 g |
| Ardamine pH | 2.7 g |
| Dextrose | 75.0 g |
| $CuSO_4.5H_2O$ | 0.00006 g |
| $ZnSO_4.7H_2O$ | 0.001 g |
| $CaCl_2.6H_2O$ | 0.0001 g |
| $FeCl_3.6H_2O$ | 0.003 g |
| $MgSO_4.7H_2O$ | 0.5 g |
| pH = 7.2 | |

Frozen vegetative mycelia (FVM) of Streptomyces avermitilis MA694 1 ATCC 55292 were prepared by inoculating 250 ml seed medium in a 2 liter 3 baffle flask with a lyophilized culture and incubating at 27° C., 85% relative humidity and 200 rpm for 16 hours. The packed cell volume of the culture was 10–15% and the pH 5.7–6.8.

Seed Cultures

To 25 ml of seed culture in a 250 ml 3 baffle flask, 1.0 ml of FVM was added and the flasks were at 27° C., 85% relative humidity and 200 rpm for 16 hours.

Biotransformation and Isolation

To 22.5 ml of biotransformation medium, 1.0 ml of seed culture was added and the flasks were incubated at 27° C., 85% relative humidity at 200 rpm for 48 hours. Then 27-OH-22,23 dihydro ivermectin B 1a aglycone (1.0 mg in 0.05 ml dimethylsulfoxide) was added and the flasks were incubated for 8 days at 27° C., 85% relative humidity and 220 rpm. Each flask was extracted with 50 ml portions of methylene chloride. The methylene chloride extracts were combined and concentrated. The resultant 27-OH avermectin disaccharides were isolated on a Dupont Zorbax ODS column using methanol: water (85:15; 80-20; 70-30) as the mobile phase. The structures of the purified avermectins were determined by NMR spectroscopy. The yield for isomer A was 10% and for isomer B was 10%, for a total yield of 20%.

STEP 3: GLYCOSYLATION AT C4"

Composition of Media

The 27-OH avennectin dissaccharides above are then glycosylated at the C4" position to yield the instant 4"-O-glucosyl 27OH avennectin B1a. The media composition, inoculum preparation and seed culture are the same as that described for Step 1.

Biotransformation and Isolation

To 40 ml of medium M102 in a 250 ml flask, 1.0 ml of seed culture was added and flasks were incubated at 30° C., 85% relative humidity at 200 rpm for 24 hours. Then 27-OH 22,23 dihydroavermectin B 1a (from Step 2 above), 1.0 mg and 0.5 ml DMSO were added and the flasks were incubated as above for 5 days. Each flask was extracted with 2×80 ml portions of $CH_2Cl_2$. The $CH_2Cl_2$ extracts were combined, concentrated and the avermectins were purified by HPLC on Dupont Zorbax ODS reverse phase columns (9.4 mm. ID×25 cm) at 60° C. using $CH_3OH:H_2O$ (80:20 or 70:30) as the mobile phase. The structures of the purified avermectins were determined by NMR. The NMR spectrum was recorded in $CDCl_3$ at ambient temperature on a Varian Unity 400 spectrometer. Chemical shifts are shown in ppm relative to internal tetramethylsilane at zero ppm.

The yields for Step 3 were 17% for isomer A and 24% for isomer B, for a total of 41%. The retention times for the 4"-O-glucosyl ivermectins on a Dupont Zorbax ODS column at 60° C. with methanol:water (80:20) as the mobile phase is as follows: isomer A 10.58 minutes and isomer B11.9 minutes. The anthelmintic and insecticidal activities of both isomers of the derivatized 27-hydroxy ivermectins are shown below in Tables 2 and 3.

The following examples are being provided in order that the instant invention may be more fully understood. Such examples are not to be construed as being limitative of the invention.

EXAMPLE 1 - HYDROXYLATION AT C27

S. erythraea (ATCC 11635, ATCC 31772 or NRRL 3887) was grown in medium M102 as described by Corcoran (Methods in Enzymology 43:487–498 1975). It contained the following in 1000 ml of distilled water: glucose, 5g; commercial brown sugar (Domino's), 10 g; tryptone, 5 g; yeast extract, 2.5 g; ethylene diamine tetraacetate, 0.036 g; betaine, 1.2 g; sodium propionate, 0.11 g. The medium was adjusted to pH 7.0–7.2 and 2.2 ml of trace elements solution which contained the following in g/l were added: $FeCl_3 \cdot 6H_2O$, 0.2; $ZnCl_2$, 0.04; $MnCl_2 \cdot 4H_2O$, 0.01; $CuCl_2 \cdot 2H_2O$, 0.01; $NaB_4O_7 \cdot 10H_2O$, 0.01; $(NH_4)_6Mo_7O_{24} \cdot 4H_2O$, 0.01.

INOCULUM PREPARATION

Frozen vegetative mycelia (FVM) were prepared by inoculating 250 ml media in a 2 liter 3 baffle flask and incubating at 32° C., 85% relative humidity and 200 RPM for 48 hours in a Kuhner cabinet. The packed cell volume of the culture was 10–12% and the pH ranged from 6.7 to 7.0. Aliquots (2 ml) of the culture were frozen, stored at −80 degrees and used as source of inoculum for future experiments.

SEED CULTURE

To 40 ml of medium M102 in a 250 ml flask, 1.0 ml of FVM was added as inoculum and the flasks were incubated at 30° C., 85% relative humidity and 200 RPM for 40 hours.

BIOTRANSFORMATION AND ISOLATION

To 40 ml of medium M102 in a 250 ml flask, 1.0 ml of seed culture was added and flasks were incubated at 30° C., 85% relative humidity at 200 RPM for 24 hours. 3.0 mg of 22, 23 dihydro avermectin aglycone in 0.1 ml DMSO were added and the flasks were incubated as above for 5 days. Each flask was extracted with 2×80 ml portions of $CH_2Cl_2$. The $CH_2Cl_2$ extracts were combined, concentrated and the avermectins were purified by HPLC on Dupont Zorbax ODS reverse phase columns (9.4 mm. ID ×25 cm) at 60° C. using $CH_3OH:H_2O$ (80:20 or 70:30) as the mobile phase. The structures of the purified avermectins were determined by mass spectroscopy and NMR spectroscopy. The NMR spectrum was recorded in $CDCl_3$ at ambient temperature on a Varian UNITY 400 spectrometer. Chemical shifts are shown in ppm relative to internal tetramethylsilane at zero ppm.

Both isomers of 27-hydroxy avermectin are produced in the same fermentation. They have significantly different retention times on HPLC, 7.63 minutes for the A isomer and 8.4 minutes for the B isomer, and are easily separated. Mass analysis indicated a molecular weight of 602.77, which is 16 mass units above the substrate, avennectin aglycone. The yields of the isomer A and isomer B were 0.6 mg and 0.48 mg, respectively.

EXAMPLE 2 - HYROXYLATION AT C27

Innoculum preparation, seed culture and biotransformation and isolation are the same as above except that avermectin B1a aglycone is substituted for 22,23 dihydro avermectin aglycone (ivermectin aglycone).

Table 4 below shows the activity profile for the instant avermectin compounds.

TABLE 4

| | Conc. mg/kg | Haemonchus Contortus | Tricho- strongulus colubriformis | Tricho- strongulus sigmodontis |
|---|---|---|---|---|
| 27-OH-22,23 dihydro B1a aglycone | | | | |
| isomer A | 1.00 | I | I | I |
| isomer B | 1.00 | I | I | I |
| 27-OH-22,23 dihydro B1a | | | | |
| isomer A | 0.25 | A | A | A |
| | 0.125 | A | A | A |
| | 0.0625 | A | A | I |
| isomer B | 0.25 | A | A | I |
| | 0.125 | A | A | I |
| | 0.0625 | MA | I | I |
| 4"-O- glucosyl, 27-OH-22,23 dihydro B1a | | | | |
| isomer A | 0.25 | A | A | A |
| | 0.125 | A | A | A |
| | 0.0625 | MA | SLA | A |
| isomer B | 0.25 | A | A | A |
| | 0.125 | MA | MA | A |

TABLE 4-continued

| | Conc. mg/kg | Haemonchus Contortus | Trichostrongulus colubriformis | Trichostrongulus sigmodontis |
|---|---|---|---|---|
| 27-OHB1a | 0.0625 | I | SLA | A |
| isomer B | 0.25 | A | A | SLA |
| | 0.125 | A | A | |
| | 0.0625 | A | A | |
| 4"-O-glucosyl, 27-OH B1a | | | | |
| isomer B | 0.25 | A | A | A |
| | 0.125 | A | A | A |
| | 0.0625 | I | I | A |
| 22,23 dihydro 8 B1a | 0.25 | A | A | A |
| | 0.125 | A | A | A |
| | 0.0625 | A | A | I |
| B1a | 0.25 | A | A | A |
| | 0.125 | A | A | A |
| | 0.0625 | A | A | SLA |

A = 85–100% effective
MA = 60–85% effective
SLA = 35–60% effective
I-inactive

What is claimed is:

1. A compound represented by Compound II or III:

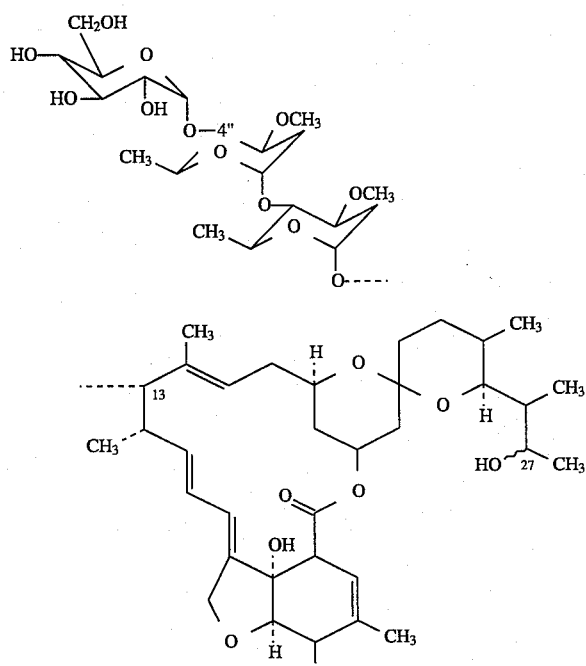

Compound II-4"-O-glucosyl-27-OH ivermectin

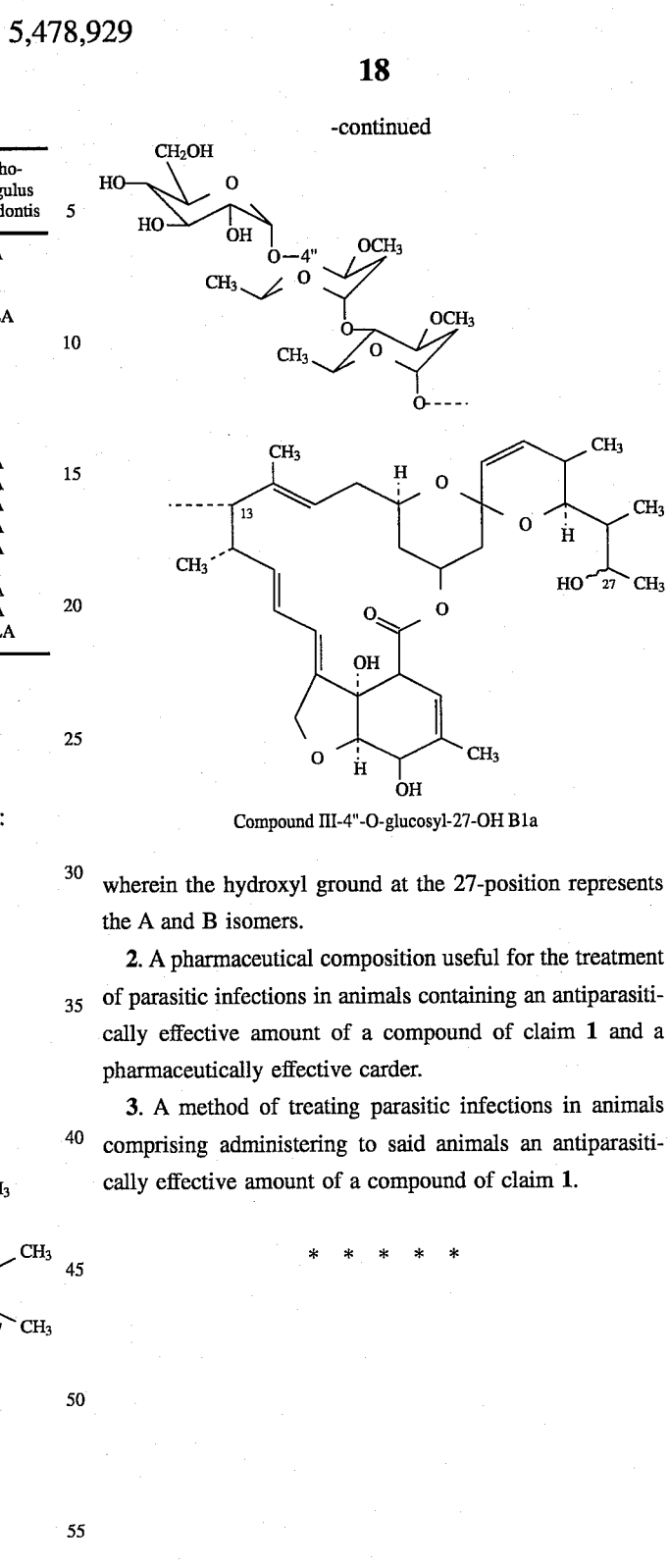

Compound III-4"-O-glucosyl-27-OH B1a wherein the hydroxyl ground at the 27-position represents the A and B isomers.

2. A pharmaceutical composition useful for the treatment of parasitic infections in animals containing an antiparasitically effective amount of a compound of claim 1 and a pharmaceutically effective carder.

3. A method of treating parasitic infections in animals comprising administering to said animals an antiparasitically effective amount of a compound of claim 1.

* * * * *

UNITED STATES PATENT AND TRADEMARK OFFICE
CERTIFICATE OF CORRECTION

PATENT NO. : 5,478,929
DATED : December 26, 1995
INVENTOR(S) : Byron H. Arison, et al.

It is certified that error appears in the above-indentified patent and that said Letters Patent is hereby corrected as shown below:

Column18, line 30:

In Claim 1, after "...wherein the hydroxyl" delete "ground" and insert in its place the word -- group --.

Column 18, line 36:
In Claim 2, after "...pharmaceutically effective" delete "carder" and insert in its place the word -- carrier --.

Signed and Sealed this

Twenty-sixth Day of March, 1996

BRUCE LEHMAN

*Attest:*

*Attesting Officer*   Commissioner of Patents and Trademarks